United States Patent [19]

Palestrant

[11] Patent Number: 5,030,201
[45] Date of Patent: Jul. 9, 1991

[54] EXPANDABLE ATHERECTOMY CATHETER DEVICE

[76] Inventor: Aubrey Palestrant, 6800 N. 47th St., Paradise Valley, Ariz. 85253

[21] Appl. No.: 441,655

[22] Filed: Nov. 24, 1989

[51] Int. Cl.[5] .............................................. A61B 17/22
[52] U.S. Cl. ...................................... 604/22; 604/29; 604/53; 128/755
[58] Field of Search ....................... 604/22, 27, 28, 51, 604/52, 53; 606/167, 168, 170, 194; 128/751, 755

[56] References Cited

U.S. PATENT DOCUMENTS

| | | |
|---|---|---|
| 679,671 | 7/1901 | Hannigan . |
| 1,155,169 | 10/1915 | Starkweather . |
| 2,816,552 | 12/1957 | Hoffman ............................ 606/170 |
| 3,557,794 | 1/1971 | Van Patten ......................... 128/345 |
| 3,670,732 | 6/1972 | Robinson ............................ 128/297 |
| 3,692,029 | 10/1972 | Adair .................................... 128/349 |
| 3,938,530 | 2/1975 | Santomieri ......................... 128/349 |
| 4,273,128 | 6/1981 | Lary ..................................... 128/305 |
| 4,465,072 | 8/1984 | Taheri ............................... 128/348.1 |
| 4,611,594 | 10/1986 | Grayhack et al. .................. 128/328 |
| 4,669,469 | 6/1987 | Gifford, III et al. ............... 128/305 |
| 4,848,000 | 5/1986 | Hershenson ......................... 128/345 |

FOREIGN PATENT DOCUMENTS

| | | |
|---|---|---|
| 0690391 | 4/1963 | United Kingdom . |
| 955490 | 4/1964 | United Kingdom . |

OTHER PUBLICATIONS

"New InterVentional Technology", *The American Journal of Cardiology;* Oct. 1, 1988, vol. 62, pp. 12F–24F.
"Recanalization of Obstructed Arteries with a Flexible, Rotating Tip Catheter"; Radiology, Nov. 1987, vol. 165; pp. 387–389, No. 2; Kensey et al.
"Removal of Focal Atheromatous Lesions By Angioscopically Guided High Speed Rotary Atherectomy", Journal of Vascular Surgery, Feb. 1988, vol. 7, No. 2, pp. 292–300, Ahn et al.

*Primary Examiner*—Richard J. Apley
*Assistant Examiner*—L. Thomas
*Attorney, Agent, or Firm*—Cahill, Sutton & Thomas

[57] ABSTRACT

An expandable atherectomy catheter device includes an expandable cutting head consisting of deformable cutting members to remove an atheroma or blood clot from a blood vessel. The cutting members, consisting of wires or blades, extend parallel to each other and are supported at the distal end of a rotatable catheter. A retraction member is slidingly disposed within the rotatable catheter and is coupled at its distal end to the cutting members; the retraction member can be manipulated from the proximal end thereof to adjust compression of the cutting members, and hence, the diameter of the cutting head. A motor is coupled to the proximal end of the rotatable catheter for rotating the cutting head to remove the atheromatous plaque or blood clot. A non-rotatable delivery catheter is inserted percutaneously within the blood vessel, and the distal end thereof is positioned proximate the site of the obstruction. The rotatable catheter extends within the delivery catheter, and the cutting head of the rotatable catheter is expanded upon being advanced to the site of the obstruction. Apparatus for aspirating the removed plaque or blood clot is also provided.

25 Claims, 3 Drawing Sheets

EXPANDABLE ATHERECTOMY CATHETER DEVICE

BACKGROUND OF THE INVENTION

1. Field of The Invention

The present invention relates generally to devices for removing atheromatous or blood clot material from blood vessels, and more particularly, to an atherectomy device adapted to be inserted percutaneously and including an expandable, rotatable cutting head as well as a method for using such a device to remove an atheroma or a blood clot.

2 Description of the Prior Art

Atheromatous material consist of fat particles and calcium deposited upon the inner walls of arteries. As these deposits increase in size, they restrict the artery lumen, reducing the flow of blood therethrough. The resulting reduction in blood flow may cause an inadequate supply of blood to reach an organ or other part of the body supplied by such artery beyond the point of restriction. If the narrowing of the artery becomes very severe, the artery may totally occlude, resulting in death of the tissue supplied by the artery, or significantly compromising tissue function.

Several methods are currently available to form a channel through a blocked artery. Initially, a guidewire was used to gently probe a channel through the blockage in the artery to reach the normal artery beyond. Once the guidewire was advanced through the blockage, an angioplasty balloon catheter was passed over the guidewire and inflated to dilate the blockage. However, this method is known to cause tears in the artery in order to accommodate the inflated balloon. Moreover, such method does not remove the atheromatous material.

More recently, efforts are being made to use laser energy to vaporize atheromatous material within a blood vessel. However, this method of using laser energy has limited application at the present time.

Several techniques have been proposed for opening a blocked artery using a catheter device to physically remove atheromatous material from the inner walls of blood vessels. For example, U.S. Pat. No. 4,669,469 (Gifford, III. et al.) describes an atherectomy catheter device having a cylindrical housing of a fixed diameter at the distal end thereof. The cylindrical housing includes a cutout on one side thereof, and a rotating cutter is slidably mounted within the cylindrical housing for cutting any deposits forced into the cutout. The cutter is rotated by a motor drive unit coupled to the cutter by a flexible drive cable. The device is advanced into a blood vessel over a guidewire. An inflatable balloon in positioned outside the cutter housing opposite the cutout to urge the housing toward the atheroma to force the atheroma into the cutout. Atheromatous material shaved from the wall of the artery is stored at the end of the cutter housing.

U.S. Pat. No. 4,273,128 (Lary) describes a surgical instrument including a pair of static cutting blades placed at the distal end of a balloon catheter to create longitudinal incisions in a narrowed or occluded artery. The static blades do not rotate, but merely create longitudinal incisions to facilitate dilation of the vessel using the inflatable balloon. The static cutting blades do not cut or shave away the atheromatous material or reduce it to a size which will permit aspiration.

U.S. Pat. No. 4,465,072 (Taheri) describes a needle catheter for scraping or thrombosing vascular walls, particularly in the treatment of varicose veins. The needle catheter includes an inflatable balloon mounted at the distal tip thereof. The balloon carries a plurality of abrasive burrs or ribs on the outer surface thereof. The catheters advance into the vessel, with the balloon initially being deflated. The balloon is then inflated, and the catheter is moved longitudinally up and down in the vessel to scrape the walls of the vessel. The function of the needle catheter is to promote thrombosis of the walls of the vein; however, scraping of the inner lining of the blood vessel causes damage thereto, making the blood vessel more prone to clotting. The described needle catheter is not intended for removing atheromatous material or blood clots from the inner walls of a blood vessel.

A catheter described by Bard includes an inner corkscrew-type guidewire which is inserted through a blocked vessel. A rotating catheter with a circumferential blade is advanced over the wire, and a core of the occluding material is removed to form a channel. Once this channel has been created, it is enlarged using a conventional dilation balloon catheter. Thus, the Bard catheter does not completely remove atheromatous material from the blood vessel. It creates a channel into which a balloon may be placed and the artery dilated. Moreover, the catheter which includes the circumferential blade is of a fixed diameter.

In "new InterVentional Technology", *The American Journal of Cardiology*, Oct. 1, 988, Volume 62, pages 12F-24F, a transluminal extraction catheter (TEC) for cutting away atherosclerotic plaque from vessel walls is described. Developed jointly by InterVentional Technologies, Inc. and Duke University's Interventional Cardiac Catheterization Program, the transluminal extraction catheter includes a motorized, rotating stainless steel element equipped with a conical cutting head. The cutting head is mounted on a flexible torque tube incorporating a vacuum system that allows retrieval of excised material. The device is controlled by a steerable guidewire. However, the diameter of the cutting head is fixed, and the size of the cutting head is limited by the size of the opening made in the blood vessel where the device is introduced.

In "Recanalization of Obstructed Arteries with a Flexible, Rotating Tip Catheter", *Radiology*, November, 1987, Volume 165, No. 2, pages 387-389, Kensey, et al. describe a catheter including a rotating cam at the distal tip rotated by an internal torsion drive wire. The rotating cam is advanced through the blockage to form a hole therethrough. Once again, however, the rotating cam is of a fixed diameter, and the size of such rotating cam is limited by the opening made in the blood vessel where the device is introduced.

In "Removal of Focal Atheromatous Lesions By Angioscopically Guided High-Speed Rotary Atherectomy", *Journal of Vascular Surgery*, February, 1988, Volume 7, No. 2, pages 292-300, Ahn, et al. describe a high-speed rotary atherectomy device inserted over a guidewire and directed with an angioscope. The atherectomy device includes a diamond-coated brass burr welded to a flexible drive shaft which rotates and tracks along a central coaxial guidewire. The drive shaft is connected to a turbine driven by compressed air. The drive shaft is encased with a protective plastic sheath. The diamond-coated brass burrs are available in various sizes selected to match the luminal diameter of the artery. The high-speed rotary burr grinds occluding atheroma into fine particles. However, the diameter of any particular selected burr is fixed and is limited by the size of the opening made in the blood vessel where the device is introduced.

While not intended to remove atheromatous material, balloon dilation catheters have long been used to dilate restricted arteries. Mechanical expandable devices are also known for re-establishing desired blood flow through a blood vessel. For example, U.S. Pat. No. 4,585,000 (Hershenson) describes an intravascular expandable device adapted to be inserted within and through the lumen of a blood vessel. The device includes a distal tip portion which may be mechanically expanded after reaching a stenotic area to dilate the vessel. Similarly, U.S. Pat. No. 3,557,794 (VanPatten) discloses a blood vessel dilation catheter using a slotted tube to form several expandible beams; a central retractor wire can be tensioned by a rotating calibrated drum to cause the beams to bow outwardly by a varying degree. However, neither of the devices disclosed by Hershenson and VanPatten are adapted to remove atheromatous material from a blood vessel, nor are they adapted to be rotated by a motor drive. Expandible devices are also known in the art for scraping the walls of a uterus, as opposed to a blood vessel. For example, U.S. Pat. Nos. 1,155,169 (Starkweather) and 3,670,732 (Robinson) both describes surgical instruments used to remove accumulated material from the walls of a uterus. The Starkweather device includes a series of expandable wires which are initially elongated during insertion, and which are thereafter compressed to form an expanded shape; the instrument is manually rotated to scrape and clean the walls of the uterus. The Robinson device uses a pair of fingers which are initially compressed within a tube during insertion The fingers are then expelled, and the device is manually rotated to wipe the fingers against the uterine wall. A vacuum source withdraws loosened material from the uterus. Clearly, the devices disclosed by Starkweather and Robinson could not be used to remove atheromatous material or blood clots from a blood vessel.

In summary, prior art atherectomy devices adapted to remove atheromatous material or blood clots from an artery all utilize a cutting member having a fixed diameter, the size of which is limited by the size of the opening in the blood vessel through which the device is introduced.

Accordingly, it is an object of the present invention to provide an expandable atherectomy catheter device having a cutting head of variable diameter to accommodate blood vessels having a wide range of internal diameters.

It is another object of the present invention to provide such an atherectomy device for cutting and aspirating atheromatous material, and which may be inserted into a blood vessel in a collapsed state to provide a narrow profile, whereby the device may be introduced into an artery using a standard angiographic percutaneous approach.

It is yet another object of the present invention to provide such an atherectomy device wherein the need for direct surgery to the blocked or narrowed vessel, or the creation of a large opening at the site of insertion into the blood vessel, can both be avoided.

It is still another object of the present invention to provide such an atherectomy device which maybe passed over a guidewire to facilitate insertion of the device into the blood vessel, and advancement of the device to the site of the blockage.

Still another object of the present invention is to provide such an atherectomy device including a coaxial catheter through which the atheromatous material, once cut from the wall of the blood vessel, may be aspirated.

Yet another object of the present invention is to provide such an atherectomy device which permits saline solution or another irrigant to be infused to the site of the cutting head while simultaneously permitting the irrigant and any dislodged atheromatous material to be aspirated.

A further object of the present invention is to provide such an atherectomy device which prevents distal embolization of atherectomized material once cut from the wall of the blood vessel.

A still further object of the present invention is to provide such an atherectomy device which may be used for removal of blood clots, with or without the addition of thrombolytic agents.

Yet another object of the present invention is to provide such an atherectomy device wherein the diameter of the cutting head may be adjusted while the cutting head is being rotated by a motor.

SUMMARY OF THE INVENTION

Briefly described, and in accordance with a preferred embodiment thereof, the present invention relates to an expandable atherectomy device for removing atheromatous material or blood clots from a blood vessel and including a first catheter having a distal end for insertion into the blood vessel and at least one elongated cutting member supported by the distal end of the first catheter and extending generally parallel to the longitudinal axis thereof. A mechanism is also provided for selectively expanding the cutting member away from the longitudinal axis of the first catheter. The first catheter includes a proximal end coupled to a motor for rotating the first catheter, and the elongated cutting member supported hereby, to cut atheromatous material or blood clots from the blood vessel.

Preferably, a plurality of such elongated cutting members are supported by the distal end of the first catheter, each extending generally parallel to the longitudinal axis thereof. The plurality of cutting members are spaced apart from one another about the longitudinal axis of the first catheter. Each of the elongated cutting members includes a first end coupled to the distal end of the first catheter, as well as an opposing second end. The mechanism for expanding the elongated cutting members is preferably a retraction member disposed with the first catheter for sliding movement therein and having a distal end secured to the second ends of the cutting members. Retraction of the retractor member selectively compresses the first and second ends of the elongated cutting members for causing the same to bow outwardly away from the longitudinal axis of the first catheter. An adjustment mechanism coupled to the proximal ends of the first catheter and the retractor member permits adjustment of the relative positions of the proximal ends of the first catheter and retractor member for adjustably varying the outward bowing of the plurality of elongated cutting members.

The aforementioned elongated cutting members may be formed of lengths of wire or strips of metal. In a preferred embodiment, a tubular metal sleeve has a plurality of longitudinal slits formed therein parallel to each other for dividing the tubular metal sleeve into a plurality of elongated metal strips. The slits preferably extend at an angle to a radial line passing through the longitudinal axis of the tubular metal sleeve for causing each of the edges of the metal strips to form a knife edge for biting into an atheroma or blood clot when the plurality of metal strips are caused to bow outwardly. The outer surface of such metal strips may also be roughened to scrape the material to be removed from the walls of the blood vessel when the cutting head is rotated.

The retractor member may simply be one or more tension wires extending within the first catheter for applying tension to the second ends of the cutting members. Preferably, the retractor member is a second catheter which is disposed within the first catheter and which rotates therewith. The second catheter includes a continuous lumen which may be passed over a guidewire. The atherectomy device of the present invention is inserted into a blood vessel through a coaxial delivery catheter in which the first catheter may be slidingly advanced and rotated. The preferred form of the present invention also includes a mechanism for aspirating particles of atheromatous material or blood clots removed by the elongated cutting members. The aspirating mechanism is in the form of a vacuum port provided at the proximal end of either the delivery catheter, the first catheter, or the second catheter (i.e., the retractor member). Preferably, saline solution or another irrigant is infused through one of the other catheters that is not being used for aspiration. The infusion rate of the saline solution is balanced with the aspiration rate to avid any net removal of fluid from the vessel. An elastic skirt may be secured to the cutting members and extending from the distal end of the first catheter to the midpoint of the cutting members; the skirt serves as a funnel to more effectively aspirate dislodged material, and further serves to direct the infused saline solution over the area being cut by the cutting head before being aspirated.

The preferred embodiment of the present invention permits adjustment of the outward bowing of the elongated cutting members, and hence adjustment of the diameter of the cutting head, while the motor is rotating the cutting head. A first drive member couples the motor to the proximal end of the first catheter, and a second drive member couples the motor to the proximal end of the retractor member. A control is provided for manipulation by the user to adjust the relative positions of the proximal ends of the first catheter and retractor member while allowing the first and second drive members to remain in engagement therewith.

The present invention also relates to the method for removing atheroma or blood clots from a blood vessel, such method including the step of inserting a delivery catheter into a blood vessel until the distal end thereof is proximate the site of the atheromatous material or blood clot. A catheter equipped with an expandable cutting head at the distal end thereof is advanced through the delivery catheter, with the cutting head thereof in a collapsed condition, until the cutting head extends beyond the distal end of the delivery catheter to the site of the atheroma or blood clot. The expandable cutting head of the cutting head catheter is then expanded to increase the diameter thereof until approximating the diameter of the blood vessel at the site of the atheroma or blood clot. The proximal end of the cutting head catheter is then rotated by a motor to rotate the expanded cutting head for removing the atheromatous material or blood clot from the walls of the blood vessel. The method of the present invention preferably includes the further step of aspirating the blood vessel proximate the cutting head to aspirate any removed portions of the atheromatous material or blood clot, preferably while infusing saline solution or another irrigant to the site of the cutting head.

DETAILED DESCRIPTION OF THE PREFERRED EMBODIMENTS

Figure 1:
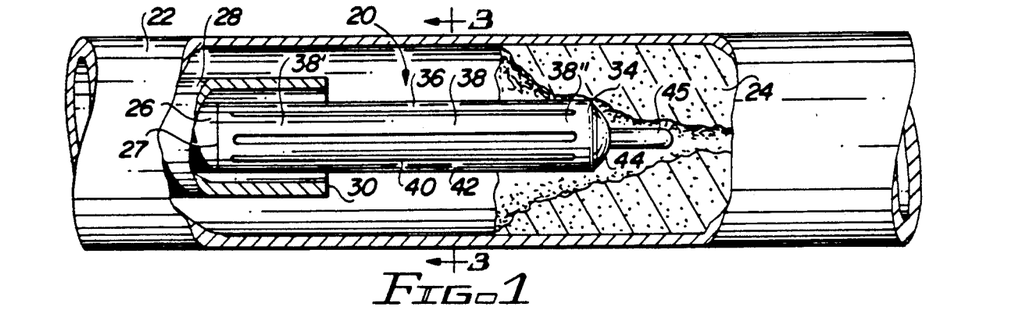
FIG. 1 is a sectioned side view of the distal end of an expandable atherectomy catheter device constructed in accordance with a first embodiment of the present invention, and shows the cutting head of the device being advanced into a portion of a blood vessel where an atheroma has formed.

In FIG. 1, the distal end of an expandable atherectomy device for removing atheroma or blood clots from a blood vessel, constructed in accordance with a first embodiment of the present invention, is designated generally by reference numeral 20. Within FIG. 1, a blood vessel 22 is shown including a formation 24 of atheromatous material or a blood clot. The expandable atherectomy device includes a first rotatable catheter 26, the distal end of which 27 is visible. First catheter 26 also includes an opposing proximal end (not shown) described in greater detail below in reference to FIGS. 13, 16, and 17. First catheter 26 may be made of a flexible, biocompatible plastic material such as polyvinyl or polyethylene, with or without a metal braided wall reinforcement.

Also shown in FIG. 1 is a delivery catheter 28 having a distal end 30 inserted within blood vessel 22. Delivery catheter 28 may be made of the same materials described above relative to first catheter 26. Delivery catheter 28 also includes an opposing proximal end (not shown) described in greater detail below in conjunction with FIGS. 13, 16, and 17. As shown in FIG. 1, first catheter 26 has an outer diameter that is slightly less than the inner diameter of delivery catheter 28 for allowing first catheter 26 to be slidingly advanced through delivery catheter 28. The distal end 27 of first catheter 26 is adapted to be inserted into the proximal end of delivery catheter 28 and advanced therethrough to the distal end 30 of delivery catheter 28. As further shown in FIG. 1, delivery catheter 28 has an outer diameter of a dimension less than the inner diameter of blood vessel 22. Distal end 30 of delivery catheter 28 is advanced through blood vessel 22 until reaching a point just ahead of atheromatous material 24. Delivery catheter 28 can be introduced percutaneously into blood vessel 22 by first positioning a guidewire (not shown) into the blood vessel using a hollow needle or other known techniques. Delivery catheter 28, initially containing a matching tapered inner catheter (not shown), may then be percutaneously introduced into blood vessel 22 over the guidewire until reaching the site of atheromatous material 24. The guidewire and inner catheter may then be withdrawn, and first catheter 26 may thereafter be advanced through delivery catheter 28.

Figure 2:
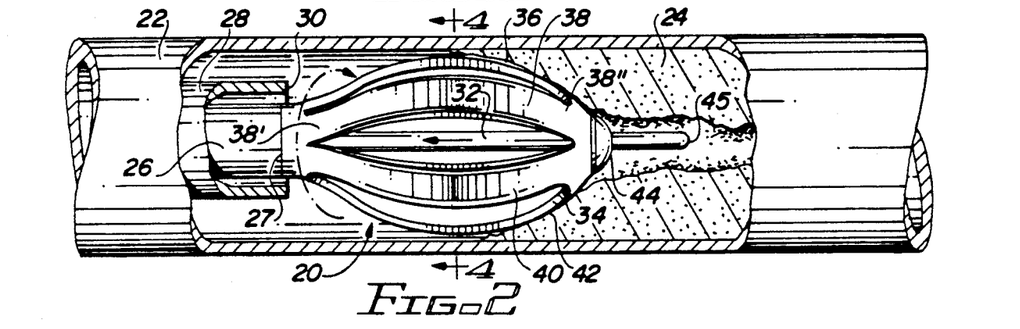
FIG. 2 is a sectioned side view of the atherectomy device shown in FIG. 1 after the cutting head has been expanded.

Visible within FIG. 2 is a central core wire, or tension wire, 32 which extends throughout the length of first catheter 26. Tension wire 32 is preferably made of stainless steel, and is disposed within the first catheter and extends generally along the central longitudinal axis thereof for sliding movement therein. Tension wire 32 includes a proximal end (described in greater detail below in conjunction with FIG. 13) which can be retracted to expand a cutting head assembly that will now be described.

Figure 3:
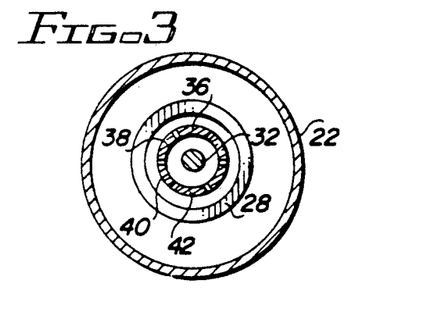
FIG. 3 is a cross-sectional view of the atherectomy device shown in FIG. 1 and taken through the plane indicated by lines 3—3 as shown in FIG. 1.
Figure 4:
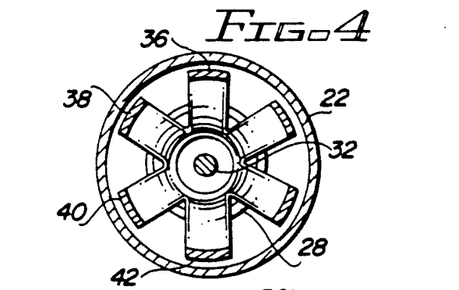
FIG. 4 is a cross-sectional view of the atherectomy device shown in FIG. 2, taken through the plane indicated by lines 4—4 in FIG. 2.

Referring to FIGS. 1-4, an expandable cutting head assembly 34 extends from and is supported by distal end 27 of first catheter 26. In FIGS. 1 and 3, cutting head assembly 34 is shown in its collapsed position, wherein the outer diameter thereof is essentially the same as the outer diameter of first catheter 26. Thus, in its collapsed position, cutting head assembly 34 appears to be a smooth extension of first catheter 26. In FIGS. 2 and 4, cutting head assembly 34 is shown in its expanded position for being rotated to cut away atheromatous material or blood clots.

Still referring to FIGS. 1-4, cutting head assembly 34 includes a plurality of elongated cutting members 36, 38, 40, and 42, each initially extending generally parallel to the longitudinal axis of first catheter 26 and surrounding tension wire 32. The plurality of cutting members 36, 38, 40, and 42 are preferably spaced apart from one another about the central longitudinal axis at uniform angular intervals. Preferably, each of the elongated cutting members shown in FIGS. 1 and 2 is formed of a strip of metal, although the cutting members may alternately be formed of lengths of steel wire. In the preferred embodiment shown in FIGS. 1-4, cutting head assembly 34 is formed by a tubular metal sleeve having a plurality of longitudinal slits formed therein generally parallel to each other for dividing the tubular metal sleeve into a plurality of elongated metal strips and thereby providing cutting members 36, 38, 40, and 42.

Still referring to FIGS. 1 and 2, each of elongated cutting members 36, 38, 40, and 42 includes first and second opposing ends. For example, elongated cutting member 38 includes a first end 38' and an opposing second end 38". The first ends of the elongated cutting members are coupled in common to distal end 27 of first catheter 26. The second ends of the elongated cutting members are each coupled in common and join with a radially extending end cap 44 having a rounded tip. If desired, a fixed leading guidewire 45 may be secured to and extend forwardly from end cap 44 to assist in passing the device through restricted areas of the blood vessel. Each of the cutting members 36, 38, 40, and 42 is relatively thin and flexible. As shown in FIGS. 2 and 4, each of elongated cutting members 36, 38, 40, and 42 is caused to bow outwardly away from the central longitudinal axis of first catheter 26 when the first and second opposing ends thereof are compressed, as by retracting end cap 44 relative to distal end 27 of first catheter 26. For this purpose, the distal end of tension wire 32 is secured to end cap 44; when tension wire 32 is retracted from its proximal end, the diameter of cutting head assembly 34 is expanded The extent of outward bowing, and hence the diameter of cutting head assembly 34, is adjustable in accordance with the degree to which the first and second opposing ends of the elongated cutting members are compressed, and hence the degree to which tension wire 32 is retracted.

Figure 5:
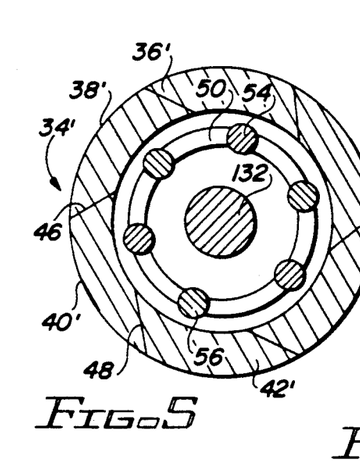
FIG. 5 is a cross-sectional view of an alternate form of cutting head for an expandable atherectomy device, shown in its collapsed condition.
Figure 6:
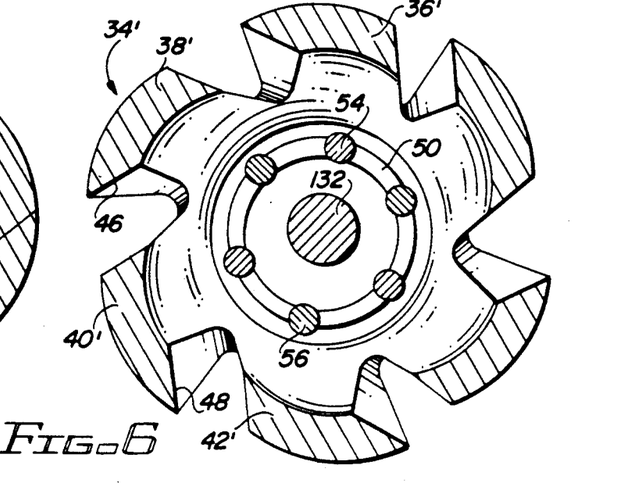
FIG. 6 is a further cross-sectional view of the cutting head shown in FIG. 5 after the same has been expanded.

Turning to FIGS. 5 and 6, an alternate form of cutting head assembly 34 is shown wherein the elongated cutting members 36', 38', 40', and 42' are formed to include knife edges, such as those designated by reference numerals 46 and 48, for biting into an atheroma or blood clot material when elongated cutting members 36', 38', 40', and 42' are bowed outwardly and rotated. Knife edges 46 and 48 each extend at an angle to a radial line passing through the longitudinal axis of the first catheter. Cutting head assembly 34' may again be formed by slitting a tubular metal sleeve longitudinally; in this event, the plurality of slits each extend at an angle to a radial line passing through the longitudinal axis of the tubular metal sleeve. Within FIGS. 5 an 6, tension wire 32 has been deleted, and a central guidewire 132 appears instead; in addition, a second inner catheter 50 and a plurality of tension wires, such as 54 and 56, are shown to expand cutting head assembly 34', as will now be explained in regard to FIGS. 11 and 12.

Figures 9, 10, 12:
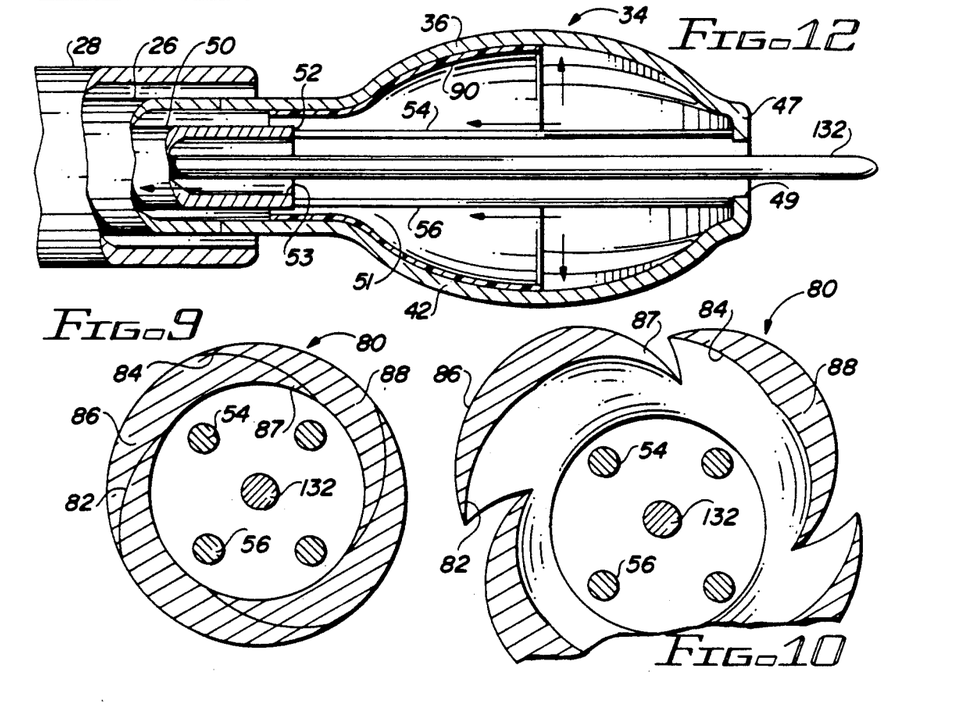
FIG. 9 is a cross-sectional view of yet another form of expandable cutting head having inwardly spiralling knife edges, shown in its collapsed condition.
FIG. 10 is a cross-sectional view of the cutting head shown in FIG. 9 after being expanded
FIG. 12 is a sectioned side view of the atherectomy device as shown in FIG. 11, but with the cutting head shown in its expanded condition, and with the aforementioned skirt deployed.
Figure 11:
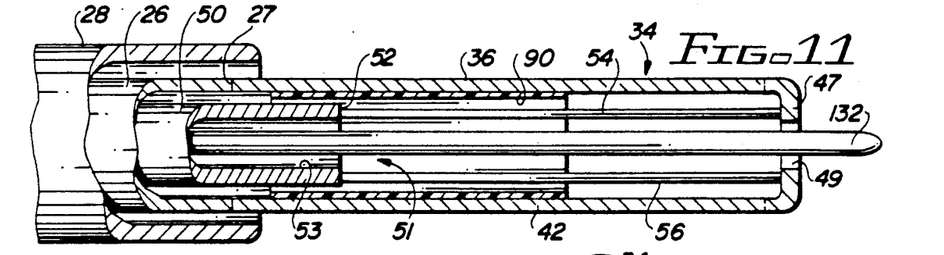
FIG. 11 is a sectioned side view of the distal end of an atherectomy device constructed in accordance with a second embodiment of the present invention wherein the device is shown in FIG. 1, adapted to receive a guidewire and includes a skirt secured to the inner walls of the cutting head.

FIGS. 11 and 12 show in side view a cutting head assembly 34' like that shown in FIGS. 5 and 6. Those features of the atherectomy device shown in FIGS. 11 and 12 which correspond with those features described in regard to FIGS. 1 and 2 are identified by like reference numerals. The atherectomy device of FIGS. 11 and 12 provides the advantage that guidewire 132 may be left in blood vessel 22, and that the entire atherectomy device, not merely delivery catheter 28, may be guided along guidewire 132 to the site of the atheromatous material or blood clot. Guidewire 132 is introduced percutaneously into blood vessel 22 using a hollow needle or other known techniques. First catheter 26 and delivery catheter 28 may then be percutaneously introduced into the blood vessel 22 over guidewire 132 until reaching the site of atheromatous material 24, using standard guidewire techniques known to those skilled in the art. Guidewire 132 extends along the central longitudinal axis of first catheter 26. End cap 47 includes a central hole 49 through which guidewire 132 passes. Guidewire 132 may be manipulated by the physician through the blockage in the artery and to the normal portion of the artery beyond the blockage. This technique both serves to help stabilize the cutting head assembly 34' when rotated by the motor, and also serves to minimize the risk of perforating the artery during rotation and advancement of the cutting head assembly.

Referring collectively to FIGS. 5, 6, 11 and 12, an elongated retractor ember 51, which includes a second inner catheter 50, surrounds central guidewire 132 and slidingly extends within first catheter 26 As shown in FIGS. 11 and 12, second catheter 50 is disposed within first catheter 26 and extends generally along the central longitudinal axis thereof for sliding movement therein. Second catheter 50 may be made of the same materials described above in regard to first catheter 26, and includes a continuous central lumen 53 for receiving guidewire 132. Second catheter 50 includes a distal end 52 which is coupled to end cap 47 by a plurality of tension wires, such as those shown as 54 and 56 for retracting end cap 47 relative to distal end 27 of first catheter 26. Tension wires 54 and 56 are preferably made of stainless steel. Alternatively, second catheter 50 may extend continuously to end cap 47, wherein distal end 52 of second catheter 50 is secured directly to end cap 44 without the use of any tension wires. As will be further explained below, the use of tension wires 54 and 56 can facilitate the use of second catheter 50 as an aspiration conduit to aspirate atheromatous material removed by the cutting head assembly. In either case, retraction of second catheter 50, and hence, retractor member 51 relative to distal end 27 of first catheter 26 causes outward bowing of the elongated cutting members in accordance with the degree of tension placed on retractor member 51 from the proximal end thereof. Retractor member 51 includes a proximal end (not shown) opposite distal end 52; the proximal end of retractor member 51 is described is greater detail below in conjunction with FIGS. 16 and 17.

Figures 7, 8:
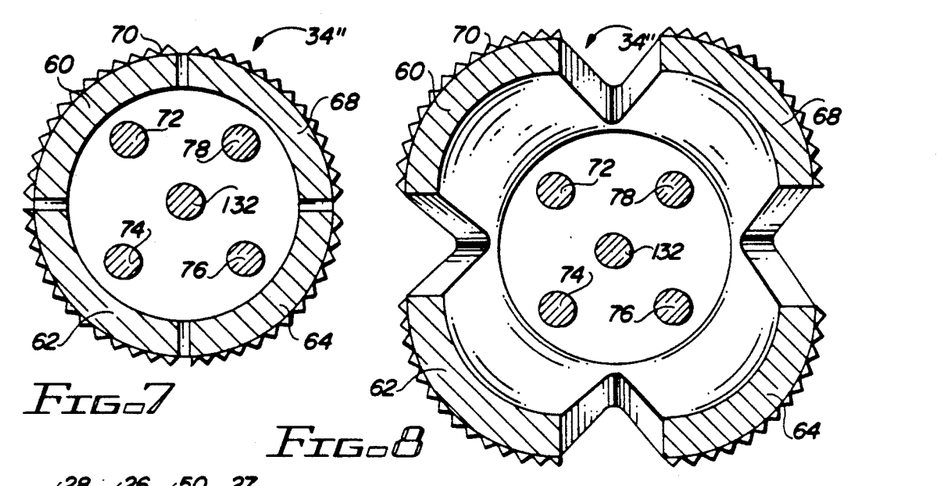
FIG. 7 is a cross-sectional view of an alternate form of cutting head having roughened outer surfaces, and shown in a collapsed condition.
FIG. 8 is a cross-sectional view of the cutting head shown in FIG. 7 after being expanded.

Referring briefly to FIGS. 7 and 8, an alternate embodiment of cutting head assembly 34 is shown and is designated by reference number 34". Cutting head assembly 34" includes a series of four elongated cutting members 60, 62, 64, and 68 each including an external surface which, in cross section, has a saw tooth pattern 70 formed upon the external surface thereof. When cutting members 60, 62, 64, and 68 are expanded by retracting tension wires 72, 74, 76, and 78, the cutting members are caused to bow outwardly, thereby causing saw tooth surfaces 70 to contact and scrape atheromatous material or blood clot material from the walls of the blood vessel as cutting head assembly 34" is rotated.

Referring briefly to FIGS. 9 and 10, yet another embodiment of a cutting head assembly is shown and is generally designated by reference numeral 80. Cutting head assembly 80 of FIGS. 9 and 10 generally resembles that shown within FIGS. 5 and 6, with the exception that the knife edges 82 and 84 of the elongated cutting members 86 and 88, respectively, spiral inwardly. The inward spiralling of knife edges 82 and 84, and hence the lessened thickness thereof near their trailing portions, is believed to provide more effective cutting action by preventing the trailing portion 87 of cutting member 86 from shielding knife edge 84 of cutting member 88. The inward spiralling of knife edges 82 and 84 is also believed to assist in guiding removed debris into the interior of cutting head assembly 80 for removal by aspiration in the manner described below.

Returning to FIGS. 11 and 12, a flexible, elastic skirt 90 is shown surrounding the interior of cutting head assembly 34 from the mid TM point of elongated cutting blades 36 and 42 to the first ends thereof proximate distal end 27 of first catheter 26. Skirt 90 functions to assist in effective removal, through aspiration, of atheromatous plaque cut from the walls of the blood vessel by cutting members 36 and 42. A source of vacuum may be connected to the proximal end (not shown) of either first catheter 26 or second catheter 50 to aspirate such dislodged material. As shown in FIG. 11, skirt 90 assumes a generally tubular form before cutting head assembly 34 is expanded. However, as shown in FIG. 12, once cutting head assembly 34 is expanded, skirt 90 also expands and assumes a funnel shape to more effectively remove dislodged plaque through aspiration.

To further enhance the removal of dislodged plaque, an irrigant such as saline solution may be infused into the vessel and discharged near the site of cutting head assembly 34. By balancing the infusion rate of the saline solution to the aspiration rate, net removal of fluid from the vessel can be brought close to zero, thereby minimizing blood loss. The saline solution is preferably infused through delivery catheter 28. Skirt 90 serves to direct the incoming saline solution toward the plaque being cut by cutting head assembly 34 to help carry away dislodged plaque; thus, skirt 90 prevents the infused saline solution from being aspirated without first passing over the forward most portions of cutting members 36 and 42.

Figures 13, 14, 15, 16:
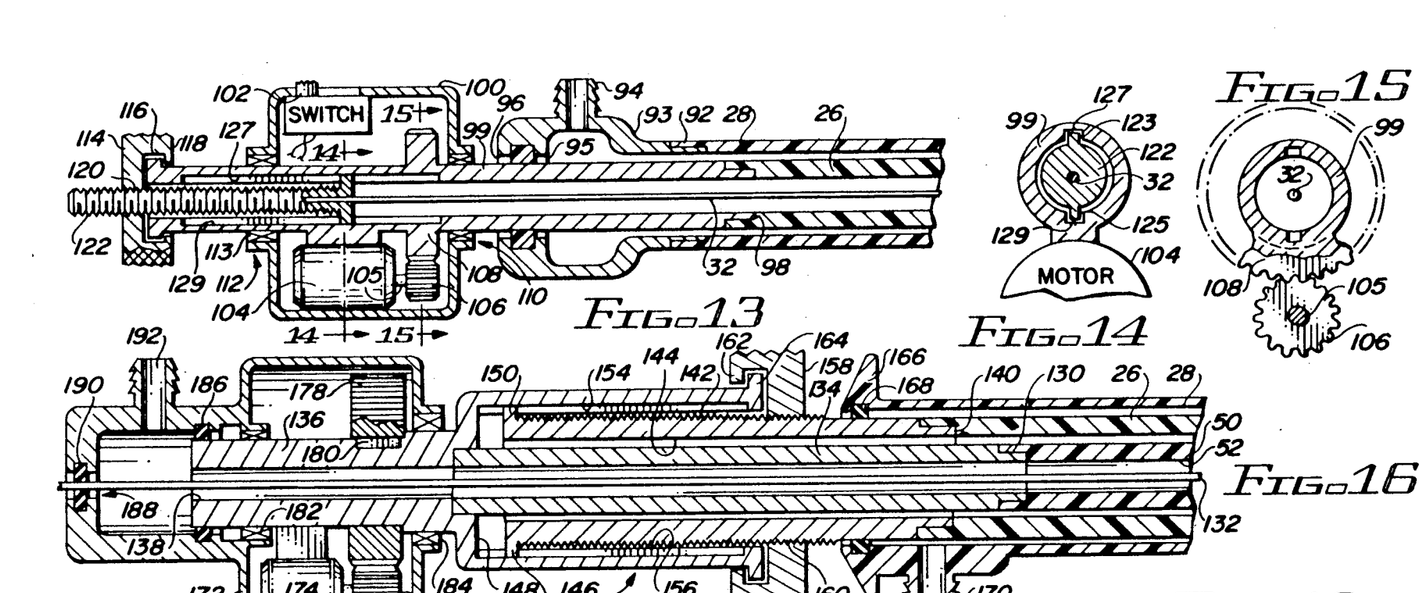
FIG. 13 is a sectioned side view of the proximal end of a first embodiment of the atherectomy device, and illustrating a motor drive unit and adjustment mechanism for controlling the atherectomy device.
FIG. 14 is a cross-sectional view of the atherectomy device shown in FIG. 13, taken through the plane indicated by lines 14—14 in FIG. 13.
FIG. 15 is a cross-sectional view of the atherectomy device shown in FIG. 13, taken through the plane indicated by lines 15—15 in FIG. 13.
FIG. 16 is a sectioned side view of an alternate embodiment of the proximal end of the atherectomy device of the present invention including a motor drive unit, a diameter adjustment control, an aspirating port and an infusion port.

In FIG. 13, the proximal end of the atherectomy device described in regard to FIGS. 1-4 is shown. Within FIG. 13, delivery catheter 28 includes a proximal end 92 that is molded to a rigid terminal member 93. Terminal member 93 includes a fluid exchange port 94 adapted to be coupled to a source of vacuum for aspirating removed material from the blood vessel. Fluid exchange port 94 may also be connected to a source of thrombolytic agents for preventing the formation of blood clots between delivery catheter 28 and first catheter 26. Terminal member 93 further includes an aperture 95 covered by an elastomeric sliding seal 96 through which first catheter 26 extends. The proximal end 98 of first catheter 26 is joined to a rigid extension tube 99 of like diameter. Elastomeric seal 96 permits first catheter 26 to be slidingly advanced through delivery catheter 28 while preventing leakage through aperture 95 between extension tube 99 and terminal member 93.

The proximal end of extension tube 99 extends within a motor drive housing 100. Included within and secured to motor drive housing 100 are an electrical slide switch 102 and an electrically operated drive motor 104. As shown in FIGS. 13 and 15, a drive gear 106 is secured to the drive shaft 105 of motor 104 and meshes with driven gear 108 which is fixedly secured to extension tube 99 for rotating first catheter 26. Accordingly, when motor 104 is operated with switch 102, first catheter 26 is rotated by motor 104 for causing the cutting head assembly at the distal end of the device to be rotated for cutting away atheromatous material. Bushing 111 is supported within a first opening 110 in a first face of motor drive unit 100 to permit extension tube 99 to rotate relative to motor drive housing 100. Similarly, bushing 113 is supported within a second circular opening 112 extending through the opposite face of motor drive housing 100 to allow the extreme proximal end of extension tube 99 to rotatably extend therethrough.

Still referring to FIG. 13, a rotatable control knob 114 freely rotates upon the end extreme proximal end of extension tube 99. An outwardly turned boss 116 formed upon the extreme proximal end of extension tube 99 cooperates with an inwardly turned boss 118 formed upon control knob 114 for preventing control knob 114 from disengaging with first catheter 26. Control knob 114 includes a threaded central aperture 120, and a threaded screw member 122 is threadedly engaged therewith. Rotation of the control knob 114 causes screw member 122 to advance or retract, depending upon the direction in which control knob 114 is turned. Tension wire 32 extends from screw member 122 to the distal end of the atherectomy device for engagement with end cap 44 (see FIGS. 1 and 2). In this embodiment, tension wire 32 serves as the retractor member, and no provision is made for insertion of a guidewire. To ensure that tension wire 32 rotates along with first catheter 26, the head of screw 122 includes a pair of keys 123 and 125 (see FIG. 14) which slidingly engage a corresponding pair of slotted channels 127 and 129 formed in the bore of extension tube 99.

Accordingly, control knob 114 and threaded screw 122 together form an adjustment means coupled to the proximal ends of first catheter 26 and tension wire 32 for adjusting the relative positions thereof, thereby adjusting the degree to which the elongated cutting members of cutting head assembly 34 are compressed for adjusting the outer diameter of cutting head assembly 34. After manually adjusting control knob 114 to obtain the desired degree of expansion of cutting head assembly 34, switch 102 is then operated to turn on motor 104 and to rotate first catheter 26, as well as tension wire 32, to rotate the cutting head assembly 34.

FIGS. 16 shows an alternate embodiment of the proximal end of the atherectomy device as would be suitable for use with the distal end shown in FIGS. 11 and 12. Within FIG. 16, second catheter 50 includes a proximal end 130 which is molded to a rigid extension tube 134 having the same diameter as second catheter 50. The opposite end of extension tube 134 is secured to a rotatable drive member 136 which includes a central bore 138 formed therein continuous with the inner lumen of extension tube 134. Second catheter 50, extension tube 134, and drive member 136 are adapted to rotate together as a unit.

Also shown in FIG. 16 is the proximal end 140 of first catheter 26. The proximal end 140 of first catheter 26 is molded to one end of extension tube 142 having an internal bore 144 of approximately the same diameter as the lumen of first catheter 26 for permitting extension tube 134 to extend therethrough.

Still referring to FIG. 16, drive member 136 includes a barrel portion 146 having a bore 148 formed therein of a diameter slightly larger than the outer diameter of extension tube 142. To insure that first catheter 26 and second catheter 50 rotate together as a unit, extension tube 142 includes a pair of keys 150 and 152 which are slidingly received within a corresponding pair of keyed slots 154 and 156 extending from bore 148 of barrel 146.

It will be recalled that an adjustment means is desired for varying the relative positions of the proximal ends of first catheter 26 and second catheter 50 to permit adjustment of the diameter of the cutting head assembly 34 (see FIGS. 11 and 12). For this purpose, a rotatable control knob 158 includes an internally threaded bore 160. Extension tube 142 is externally threaded and threadingly engages bore 160 of control knob 158. Control knob 158 includes a downwardly turned boss 162 which cooperates with upwardly turn boss 164 of barrel 146 to permit control knob 158 to be freely rotated relative to barrel 146 without becoming disengaged therefrom. As control knob 158 is rotated, the position of extension tube 142 relative to drive member 136 is varied, thereby adjusting the relative positions of the proximal ends of first catheter 26 and second catheter 50. Such adjustments are made while the motor drive mechanism is turned off.

Also shown in FIG. 16 is delivery catheter 28. The proximal end 166 of delivery catheter 28 includes an elastomeric seal 168 which sealingly engages against a smooth portion of the outer wall of extension tube 142. Accordingly, first catheter 26 and second catheter 50 may be slidingly advanced or retracted as a unit within delivery catheter 28 while maintaining a fluid-type seal between delivery catheter 28 and first catheter 26. Proximal end 166 of delivery catheter 28 further includes an infusion port 170 which may be used to infuse saline solution or another irrigant into the lumen of delivery catheter 28 for delivery into the blood vessel at the distal end of delivery catheter 28, in the manner described above.

As further shown in FIG. 16, drive member 136 extends within a motor drive housing 172 containing a motor 174 secured thereto and further including an operating switch (not shown). Drive gear 176 is secured to the driveshaft of motor 174. Driven gear 178 is secured by key 180 to drive member 136 and meshes with drive gear 176 for rotating both first catheter 26 and second catheter 50 when motor 174 is operated. Motor housing 172 includes a pair of bushings 182 and 184 which permit drive member 136 to freely rotate within motor drive housing 172. In addition, an elastomeric O-ring seal 186 forms a fluid-tight seal around drive member 136. Further, motor drive housing 172 includes a central aperture 188 coaxial with bore 138 of drive member 136. Aperture 188 is sealed by an elastomeric split diaphragm 190 to permit the free passage of guidewire 132 there through.

Figures 17, 18:
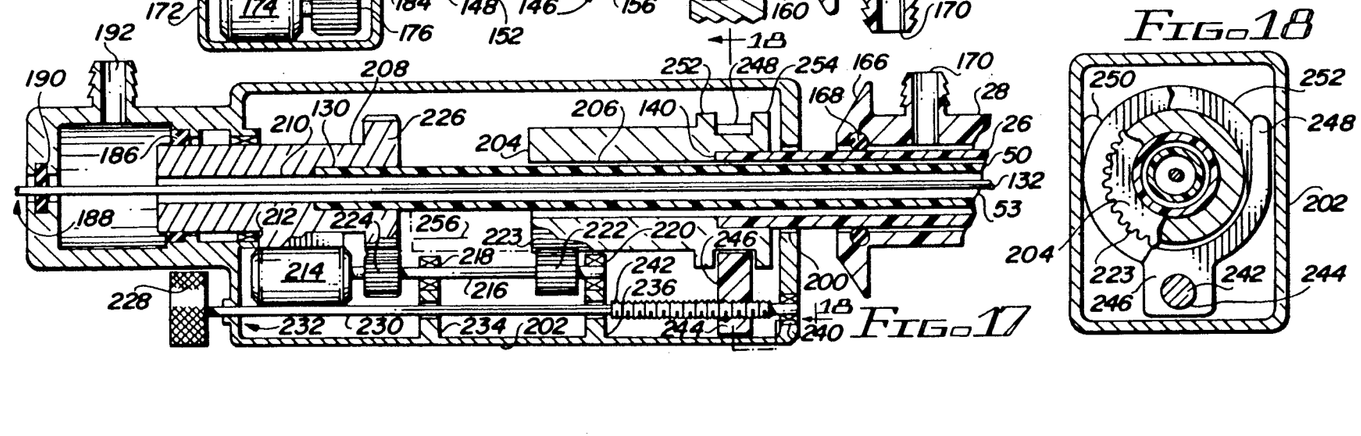
FIG. 17 is a sectioned side view of a third embodiment of the proximal end of an atherectomy device of the present invention and including a motor drive unit and diameter adjustment mechanism permitting adjustment of the cutting head diameter while the motor unit is operating.
FIG. 18 is a cross-sectional view of the motor drive unit shown in FIG. 17 taken through the plane designated by lines 18-18 within FIG. 17.

To facilitate aspiration of dislodged atheromatous material or blood clot material, motor drive housing 172 further includes an aspiration port 192 adapted to be coupled to a source of vacuum. Such dislodged material is aspirated through the lumen of second catheter 50, through the lumen of extension tube 134, and through bore 138 of drive member 136 to aspiration port 192. Refering to FIGS. 17 and 18, a third embodiment of the proximal end of the atherectomy device is shown. Like the device shown in FIG. 16, the device shown in FIGS. 17 and 18 is suitable for use with the distal end shown in FIGS. 11 and 12. The device shown in FIGS. 17 and 18 is capable of varying the external diameter of cutting head assembly 34 (see FIG. 12) while the motor drive is operating. Within FIG. 17, delivery catheter 28 is again shown including a proximal end 166, and elastomeric O-ring seal 168, and an infusion port 170. First catheter 26 extends through the distal end 166 of delivery catheter 28 and extends through an aperture 200 of motor drive housing 202. The proximal end 140 of first catheter 26 is secured to a rotatable drive member 204 disposed within motor drive housing 202. Rotatable drive member 204 includes a central bore 206 of the same internal diameter as that of first catheter 26 for allowing second catheter 60 to extend therethrough.

Like first catheter 26, second catheter 50 also extends within motor drive housing 202; the proximal end 130 of second catheter 50 is secured to a second rotatable drive member 208 which includes a central bore 210 having an internal diameter corresponding to that of the lumen of second catheter 50. Rotatable drive member 208 is rotatably supported within motor drive housing 202 by a bushing 212. Elastomeric seal 186 forms a fluid-tight seal between motor drive housing 202 and drive member 208. Split diaphragm seal 190 seals central aperture 188 within motor drive housing 202 while permitting guidewire 132 to be inserted therethrough. Motor drive housing 202 further includes an aspiration port 192 for aspirating dislodged plaque through the lumen of second catheter 50 and through bore 210 of drive member 208.

As shown in FIG. 17, motor 214 is disposed within motor drive housing 202 and is secured thereto. Motor 214 rotates driveshaft 216 which is supported by bushings 218 and 220. A first drive gear 222 is secured to driveshaft 216 for rotation therewith. Drive gear 222 meshes with an outer geared surface 223 of drive member 204 for rotating first catheter 26. Similarly, a second drive gear 224 is secured to driveshaft 216 for rotation therewith. Drive member 208 includes an enlarged shoulder portion 226 having a geared peripheral surface which meshes with drive gear 224 in order to rotate second catheter 50 at the same rotational speed as first catheter 26.

It will be recalled that an adjustment mechanism is desired for adjusting the relative positions of proximal end 140 of first catheter 26 and proximal end 130 of second catheter 50 relative to each other to adjust the diameter of the cutting head assembly. For this purpose, an adjustment knob 228 is supported upon motor drive housing 202 for rotating shaft 230. Shaft 230 extends through aperture 232 of motor drive housing 232, and through a pair of support brackets 234 and 236 within a front face of motor drive housing 202. The end of shaft 230 opposite control knob 228 is rotatably supported by a bushing 240 supported within motor drive housing 202.

Referring to FIGS. 17 and 18, shaft 230 includes a threaded portion 242 which is threadingly engaged with aperture 244 of a moveable control block 246. Control block 246 includes a pair of support arms 248 and 250 which extend upwardly and around drive member 204. A pair of radial flanges 252 and 254 extend outwardly from drive member 204 on opposing sides of support arms 248 and 250 to form a sliding loose fit therewith. Rotation of control knob 228 causes control block 246 to move forwardly or rearwardly, depending upon the direction in which control knob 228 is rotated. As control block 246 is moved, rotatable drive member 204 is also caused to advance or retract, as indicated by the directional arrow labeled 256. Drive gear 222 remains constantly meshed with the outer geared surface 223 of drive member 204, and accordingly, control knob 228 may be rotated even while motor 214 is operating.

Those skilled in the art will now appreciate that an improved atherectomy device has been described including an adjustable cutting head assembly which may be used to remove atheromatous material or blood clot material from blood vessels widely ranging diameters. While the present invention has been described with reference to several preferred embodiments thereof, the description is for illustrative purposes only and is not to be construed as limiting the scope of the invention. Various modifications and changes may be made by those skilled in the art without departing from the true spirit and scope of the invention as defined by the appended claims.

I claim:

1. An expandable atherectomy device for removing atheroma or blood clots from a blood vessel, comprising in combination:
    a. a first catheter having a distal end to be inserted into a blood vessel and having an opposing proximal end, said first catheter extending along a central longitudinal axis, said first catheter being flexible for allowing said atherectomy device to be guided through a blood vessel, said first catheter having a central lumen of a predetermined internal diameter extending from the proximal end thereof to the distal end thereof;
    b. at least one elongated cutting member supported by the distal and of said first catheter and extending generally parallel to the longitudinal axis of said first catheter;
    c. expansion means coupled to said at least one cutting member and extending through the central lumen of said first catheter for selectively expanding said at least one elongated cutting member away from the longitudinal axis of said first catheter;
    d. a motor coupled to the proximal end of said first catheter for rotating said first catheter and said at least one cutting member to remove atheromatous material or a blood clot from a blood vessel; and
    e. one of said first catheter and said expansion means including means for permitting fluids to be passed within said first catheter between the proximal end of said first catheter and the distal end thereof.

2. An expendable atherectomy device as recited by claim 1 including a plurality of elongated cutting members supported by the distal end of said first catheter and each extending generally parallel to the longitudinal axis of said first catheter and spaced apart from one another about said longitudinal axis, each of said plurality of elongated cutting members being coupled to said expansion means for being selectively expanded away from the longitudinal axis of said first catheter, and each of said plurality of elongated cutting members being rotated by said motor to remove an atheromatous material or a blood clot from a blood vessel.

3. An expandable atherectomy device as recited by claim wherein said plurality of elongated cutting members each have first and second opposing ends, the first ends of said plurality of elongated cutting members being coupled in common to the distal end of said first catheter, the second ends of said plurality of elongated cutting members being coupled in common to said expansion means, said expansion means selectively compressing the first ends and second ends of said plurality of elongated cutting members together for causing each of said plurality of elongated cutting members to bow outwardly away from the longitudinal axis of said first catheter.

4. An expandable atherectomy device as recited by claim 3 wherein said expansion means adjustably compresses the first ends and second ends of said plurality of elongated cutting members for adjustably varying the outward bowing of said plurality of elongated cutting members.

5. An expandable atherectomy device as recited by claim 1 including a delivery catheter having a distal end to be inserted into a blood vessel and having an opposing proximal end, the distal end of said first catheter being adapted to be inserted into said delivery catheter through the proximal end thereof and advanced therethrough to the distal end thereof.

6. An expandable atherectomy catheter device for removing atheroma or blood clots from a blood vessel, comprising in combination:
   a. a first rotatable catheter having a distal end to be inserted into a blood vessel and having an opposing proximal end, said first rotatable catheter extending along a central longitudinal axis, said first catheter being flexible for allowing said atherectomy device to be guided through a blood vessel, said first catheter having a central lumen of a predetermined internal diameter extending from the proximal end thereof to the distal end thereof;
   b. at least one elongated cutting member extending generally parallel to the central longitudinal axis of said first rotatable catheter, said cutting member having first and second opposing ends, the first end of said at least one cutting member being coupled to the distal end of said first catheter, said at least one cutting member being flexible to bow outwardly away from the central longitudinal axis of said first catheter when the first and second ends of said at least one cutting member are compressed;
   c. an elongated flexible retractor member generally disposed within said first catheter and extending through the central lumen of said first catheter and extending generally along the central longitudinal axis thereof for sliding movement therein, said retractor member having a distal end coupled to the second end of said at least one cutting member and having an opposing proximal end;
   d. adjustment means coupled to the proximal ends of said first catheter and said retractor member for adjusting the relative positions of the proximal ends of said first catheter and said retractor member along the central longitudinal axis of said first catheter, and thereby adjusting the distance between the first and second ends of said at least one cutting member for adjusting the amount by which said at least one cutting member bows outwardly;
   e. a motor coupled to the proximal end of said first catheter for rotating said first catheter and said at least one cutting member to remove atheromatous material or a blood clot from a blood vessel; and
   f. one of said first catheter and said retractor member including means for permitting fluids to be passed within said first catheter between the proximal end of said first catheter and the distal end thereof.

7. An expandable atherectomy catheter device as recited by claim 6 including a plurality of elongated cutting members supported by the distal end of said first catheter and each extending generally parallel to the longitudinal axis of said first catheter and spaced apart from one another about said longitudinal axis, each of said plurality of elongated cutting members having first and second opposing ends, the first end of each said cutting member being coupled to the distal end of said first catheter, each of said cutting members being flexible to bow outwardly away from the central longitudinal axis of said first catheter when the first and second ends thereof are compressed, the second end of each of said plurality of cutting members being coupled to the distal end of said retractor member, said retractor member and said adjustment means selectively causing each of said plurality of cutting members to bow outwardly by an adjustable amount, and each of said plurality of elongated cutting members being rotated by said motor to remove atheromatous material or a blood clot from a blood vessel.

8. An expandable atherectomy catheter device as recited by claim 7 wherein said plurality of elongated cutting members are each formed of a length of wire.

9. An expandable atherectomy catheter device as recited by claim 7 wherein said plurality of elongated cutting members are each formed of a strip of metal.

10. An expandable atherectomy catheter device as recited by claim 7 wherein said plurality of elongated cutting members are formed by a tubular metal sleeve having a plurality of longitudinal slits formed therein generally parallel to each other for dividing said tubular metal sleeve into a plurality of elongated metal strips.

11. An expandable atherectomy catheter device as recited by claim 10 wherein said tubular metal sleeve has a longitudinal axis coaxial with the central longitudinal axis of said first catheter and wherein said plurality of slits each extend at an angle to a radial line passing through the longitudinal axis of said tubular metal sleeve for causing the edges of said plurality of elongated cutting members to form a knife edge for biting into an atheroma or blood clot when said elongated cutting members bow outwardly.

12. An expandable atherectomy catheter device as recited by claim 7 wherein said plurality of elongated cutting members each include a roughened outer surface for scraping atheromatous material or a blood clot when said elongated cutting members bow outwardly.

13. An expandable atherectomy catheter device as recited by claim 7 wherein said elongated retractor member comprises a second catheter disposed within said first catheter.

14. An expandable atherectomy catheter device as recited by claim 13 wherein said second catheter includes a continuous central lumen for receiving a guidewire.

15. An expandable atherectomy catheter device as recited by claim 7 wherein said elongated retractor member comprises a tension wire.

16. An expandable atherectomy catheter device as recited by claim 13 wherein said first catheter has a predetermined outer diameter, said atherectomy device further including a delivery catheter having an open distal end to be inserted into a blood vessel and having an opposing proximal end, said delivery catheter having a central lumen of a second predetermined inner diameter larger than the outer diameter of said first catheter for allowing said first catheter to be received within said delivery catheter, the distal end of said first catheter being adapted to be inserted into the central lumen of said delivery catheter through the proximal end of said delivery catheter and advanced therethrough to the pen distal end of said delivery catheter.

17. An expandable atherectomy catheter device as recited by claim 16 further including aspirating means coupled to the proximal end of one of said first catheter, second catheter, or delivery catheter, for aspirating atheromatous material or blood clot material cut by said plurality of elongated cutting members.

18. An expandable atherectomy catheter device as recited by claim 17 wherein said aspirating means is coupled to the proximal end of said second catheter, the distal end of said second catheter having an opening formed therein to aspirate portions of an atheroma or blood clot removed by said plurality of elongated cutting members.

19. An expandable atherectomy device as recited by claim 18 wherein said delivery catheter includes an infusion port coupled to the proximal end of said delivery catheter for infusing an irrigant to the distal end of said delivery catheter to assist in the removal of atheromatous material or blood clot material cut by said plurality of elongated cutting members.

20. An expandable atherectomy device as recited by claim 16 including an elastic skirt secured top said plurality of elongated cutting members and extending from the first ends of said plurality of elongated cutting members to approximately the central portions of said plurality of cutting members, said elastic skirt expanding to form a funnel shape when said plurality of cutting members are expanded, said atherectomy device further including aspirating means coupled to the proximal end of one of said first and second catheters for aspirating atheromatous material or blood clot material cut by said plurality of elongated cutting members, said elastic skirt collecting dislodged atheromatous material or blood clot material for aspiration.

21. An expandable atherectomy catheter device as recited by claim 7 including first drive means for coupling said motor to the proximal end of said first catheter for rotating said first catheter, and including second drive means for coupling said motor to the proximal end of said retractor member for rotating said retractor member, and wherein said adjustment means includes a control for manipulation by a user to adjust the outward bowing of said plurality of elongated cutting members while said motor is operating.

22. A method for removing atheroma or blood clots from a blood vessel, said method comprising in combination the steps of:
  a. inserting a delivery catheter into a blood vessel until the distal end thereof is proximate the site of the atheroma or blood clot;
  b. inserting into the delivery catheter a cutting head catheter having an expandable cutting head at the distal end thereof, and advancing the distal end of the cutting head catheter through the delivery catheter and out the distal end thereof to the site of the atheroma or blood clot, with the expandable cutting head in a collapsed condition;
  c. expanding the cutting head of the cutting head catheter to increase the diameter thereof until approximating the diameter of the blood vessel at the site of the atheroma or blood clot; and
  d. rotating the proximal end of the cutting head catheter to rotate the cutting head and remove the atheroma or blood clot.

23. The method recited by claim 22 including the further step of aspirating the blood vessel proximate the site of the cutting head to aspirate portions of the atheroma or blood clot removed by the cutting head.

24. The method recited by claim 23 including the further step of infusing an irrigant into the blood vessel proximate the site of the cutting head to help carry away dislodged portions of the atheroma or blood clot by said aspirating step.

25. The method recited by claim 24 wherein the irrigant is infused at approximately the same rate that the blood vessel is aspirated to minimize loss of blood from the blood vessel.

* * * * *